(12) United States Patent
Haller et al.

(10) Patent No.: US 8,594,799 B2
(45) Date of Patent: Nov. 26, 2013

(54) COCHLEAR ELECTRODE INSERTION

(75) Inventors: Matthew I. Haller, Valley Village, CA (US); Edward H. Overstreet, Valencia, CA (US)

(73) Assignee: Advanced Bionics, Valencia, CA (US)

( * ) Notice: Subject to any disclaimer, the term of this patent is extended or adjusted under 35 U.S.C. 154(b) by 561 days.

(21) Appl. No.: 12/610,000

(22) Filed: Oct. 30, 2009

(65) Prior Publication Data

US 2010/0114288 A1    May 6, 2010

Related U.S. Application Data

(60) Provisional application No. 61/110,463, filed on Oct. 31, 2008.

(51) Int. Cl.
*A61N 1/00* (2006.01)

(52) U.S. Cl.
USPC .................................................. 607/57

(58) Field of Classification Search
USPC .................................................. 607/57, 137
See application file for complete search history.

(56) References Cited

U.S. PATENT DOCUMENTS

| | | |
|---|---|---|
| 3,751,605 A | 8/1973 | Michelson |
| 4,400,590 A | 8/1983 | Michelson |
| 4,865,037 A | 9/1989 | Chin et al. |
| 4,940,050 A | 7/1990 | Forssmann et al. |
| 5,045,662 A | 9/1991 | Yamada |
| 5,300,106 A | 4/1994 | Dahl et al. |
| 5,396,902 A | 3/1995 | Brennen et al. |
| 5,443,493 A | 8/1995 | Byers et al. |

(Continued)

FOREIGN PATENT DOCUMENTS

| | | |
|---|---|---|
| EP | 1754509 B1 | 6/2009 |
| EP | 2113283 A1 | 11/2009 |

(Continued)

OTHER PUBLICATIONS

Thomas Roland Jr, "A Model for Cochlear Implant Electrode Insertion and Force Evaluation: Results with a New Electrode Design and Insertion Technique," The Laryngoscope, 115, Aug. 2005, pp. 1325-1339.

(Continued)

*Primary Examiner* — Christopher D Koharski
*Assistant Examiner* — Nadia Ahmad
(74) *Attorney, Agent, or Firm* — Steven L. Nichols; R. Camden Robinson; Van Cott, Bagley, Cornwall & McCarthy P.C.

(57) ABSTRACT

A system for mechanically assisted insertion of an electrode includes: an insertion tool configured to insert the electrode into biological tissues; and a controller configured to control the insertion tool, in which the controller is further configured to select operating parameters comprising a maximum allowable force profile from a library of operating parameters, in which the maximum allowable force profile is generated from data recorded during a number of previous successful operations. Also, a method for insertion of a cochlear lead, includes: selecting operating parameters comprising a maximum allowable force profile from a library of operating parameters; inserting the cochlear lead while sensing real time force and position; and continuing the insertion while the real time force is below the maximum allowable force profile, in which the maximum allowable force profile is generated from data recorded during a number of previous successful operations.

22 Claims, 8 Drawing Sheets

(56) References Cited

U.S. PATENT DOCUMENTS

| | | | |
|---|---|---|---|
| 5,507,725 | A | 4/1996 | Savage et al. |
| 5,623,582 | A | 4/1997 | Rosenberg |
| 5,626,629 | A | 5/1997 | Faltys et al. |
| 5,771,902 | A | 6/1998 | Lee et al. |
| 5,784,542 | A | 7/1998 | Ohm et al. |
| 5,876,373 | A | 3/1999 | Giba et al. |
| 5,938,691 | A | 8/1999 | Schulman et al. |
| 5,964,714 | A | 10/1999 | Lafontaine |
| 6,038,484 | A | 3/2000 | Kuzma |
| 6,067,474 | A | 5/2000 | Schulman et al. |
| 6,070,105 | A | 5/2000 | Kuzma |
| 6,077,244 | A | 6/2000 | Botich et al. |
| 6,096,004 | A | 8/2000 | Meglan et al. |
| 6,112,124 | A * | 8/2000 | Loeb .......................... 607/137 |
| 6,112,598 | A | 9/2000 | Tenerz et al. |
| 6,119,044 | A | 9/2000 | Kuzma |
| 6,125,302 | A | 9/2000 | Kuzma |
| 6,129,753 | A | 10/2000 | Kuzma |
| 6,144,883 | A | 11/2000 | Kuzma |
| 6,157,861 | A * | 12/2000 | Faltys et al. .................... 607/57 |
| 6,167,763 | B1 | 1/2001 | Tenerz et al. |
| 6,203,485 | B1 | 3/2001 | Urick |
| 6,249,704 | B1 | 6/2001 | Maltan et al. |
| 6,272,371 | B1 | 8/2001 | Shlomo |
| 6,289,247 | B1 | 9/2001 | Faltys et al. |
| 6,358,281 | B1 | 3/2002 | Berrang et al. |
| 6,390,970 | B1 | 5/2002 | Muller |
| 6,493,573 | B1 | 12/2002 | Martinelli et al. |
| 6,671,550 | B2 | 12/2003 | Iaizzo et al. |
| 6,748,255 | B2 | 6/2004 | Fuimaono et al. |
| 6,970,730 | B2 | 11/2005 | Fuimaono et al. |
| 6,973,340 | B2 | 12/2005 | Fuimaono et al. |
| 6,976,965 | B2 | 12/2005 | Corl et al. |
| 7,097,620 | B2 | 8/2006 | Corl et al. |
| 7,257,434 | B2 | 8/2007 | Fuimaono et al. |
| 7,449,002 | B1 | 11/2008 | Wenstad |
| 7,472,601 | B1 | 1/2009 | Tenerz et al. |
| 8,260,437 | B2 | 9/2012 | Llinas et al. |
| 2001/0049466 | A1 | 12/2001 | Leysieffer et al. |
| 2002/0012438 | A1 | 1/2002 | Leysieffer et al. |
| 2002/0032391 | A1 | 3/2002 | McFann et al. |
| 2002/0042632 | A1 | 4/2002 | Iaizzo et al. |
| 2002/0103446 | A1 | 8/2002 | McFann et al. |
| 2002/0161114 | A1 | 10/2002 | Gunatillake et al. |
| 2003/0040684 | A1 | 2/2003 | Soukup et al. |
| 2003/0159518 | A1 | 8/2003 | Sawatari et al. |
| 2005/0085715 | A1 | 4/2005 | Dukesherer et al. |
| 2005/0085720 | A1 | 4/2005 | Jascob et al. |
| 2005/0171508 | A1 | 8/2005 | Gilboa |
| 2005/0234535 | A1 | 10/2005 | Risi et al. |
| 2005/0268724 | A1 | 12/2005 | Tenerz |
| 2006/0089569 | A1 | 4/2006 | Soukup et al. |
| 2006/0094982 | A1 | 5/2006 | Corl et al. |
| 2006/0167472 | A1 | 7/2006 | Hong et al. |
| 2006/0241505 | A1 | 10/2006 | Ahmed et al. |
| 2006/0293643 | A1 | 12/2006 | Wallace et al. |
| 2007/0016067 | A1* | 1/2007 | Webster et al. .............. 600/464 |
| 2007/0197896 | A1 | 8/2007 | Moll et al. |
| 2007/0225787 | A1* | 9/2007 | Simaan et al. .............. 607/137 |
| 2008/0077049 | A1 | 3/2008 | Hirshman |
| 2008/0127065 | A1 | 5/2008 | Bryant et al. |
| 2008/0147173 | A1 | 6/2008 | Mciff et al. |
| 2008/0154339 | A1 | 6/2008 | Carter |
| 2008/0200928 | A1 | 8/2008 | Savall Calvo et al. |
| 2009/0012422 | A1 | 1/2009 | Marban |
| 2009/0088650 | A1 | 4/2009 | Corl |
| 2009/0259140 | A1 | 10/2009 | Buchman et al. |
| 2010/0049318 | A1 | 2/2010 | Jolly et al. |
| 2010/0094311 | A1 | 4/2010 | Jolly et al. |
| 2010/0114288 | A1 | 5/2010 | Haller et al. |
| 2010/0125311 | A1 | 5/2010 | Choi et al. |
| 2012/0071890 | A1 | 3/2012 | Taylor et al. |
| 2012/0172893 | A1 | 7/2012 | Taylor et al. |
| 2012/0310258 | A1 | 12/2012 | Llinas et al. |

FOREIGN PATENT DOCUMENTS

| | | | |
|---|---|---|---|
| WO | 94014494 | A2 | 7/1994 |
| WO | 0032105 | | 6/2000 |
| WO | 0126734 | A1 | 4/2001 |
| WO | 0180922 | A2 | 11/2001 |
| WO | 0180922 | A3 | 11/2001 |
| WO | 03049658 | A1 | 6/2003 |
| WO | 2004045363 | A2 | 6/2004 |
| WO | 2004045363 | A3 | 6/2004 |
| WO | 2005004760 | A1 | 1/2005 |
| WO | 2005009215 | A2 | 2/2005 |
| WO | 2005084122 | A2 | 9/2005 |
| WO | 2005084122 | A3 | 9/2005 |
| WO | 2006027781 | A2 | 3/2006 |
| WO | 2006027781 | A3 | 3/2006 |
| WO | 2006048097 | A1 | 5/2006 |
| WO | 2006118915 | A2 | 11/2006 |
| WO | 2006118915 | A3 | 10/2007 |
| WO | 2009070616 | A2 | 6/2009 |
| WO | 2009124287 | A1 | 10/2009 |
| WO | 2009070616 | A3 | 1/2010 |
| WO | 2010042611 | A1 | 4/2010 |
| WO | 2010053673 | A2 | 5/2010 |
| WO | 2010053673 | A3 | 7/2010 |
| WO | 2011053766 | A1 | 5/2011 |
| WO | 2012010783 | A1 | 1/2012 |
| WO | 2012040297 | A2 | 3/2012 |
| WO | 2012040297 | A3 | 3/2012 |
| WO | 2012040355 | A2 | 3/2012 |
| WO | 2012040355 | A3 | 6/2012 |
| WO | 2012168921 | A2 | 12/2012 |
| WO | 2013038363 | A2 | 3/2013 |

OTHER PUBLICATIONS

"Medic Vision Ltd Utilizes SensAble Technologies' Haptic Devices to Deliver Realistic Surgical Drilling Training: Touch-enabled Simulators Provide Unlimited Practice for Better ENT Specialist Training, Improved Patient Outcomes and Safety," May 7, 2008, http://www.prweb.com/releases/sensable/medic_vision/prweb924954.htm.

"Cochlear Implant Electrode Design and Preservation of Residual Hearing," Andreas Jäger et al., Feb. 2, 2008 http://www.medel.com.ar/ENG/US/50_Resources/30_Conference_presentations/30_Manchester_Sept_2002/110_manchester_residual.asp.

Catherine A. Todd et al., "Force Application During Cochlear Implant Insertion: An Analysis for Improvement of Surgeon Technique," IEEE Transactions on Biomedical Engineering, vol. 54, No. 7, Jul. 2007, pp. 1247-1255.

Kurt E. Petersen, Proc IEEE, vol. 70, 420 (1982) http://www-inst.eecs.berkeley.edu/~n245/fa01/PETERSON.PDF.

Johnson; Microfabrication of Biocompatible Stimulation Electrode Arrays for Cochlear Implants; 24th Annual Microelectronic Engineering Conference, May 2006.

Wise et al; Microelectrodes, Microelectronics, and Implantable Neural Microsystems; Proceedings of the IEEE, vol. 96, No. 7, p. 1184-1202, Jul. 2008.

Bell et al; a Flexible micromachined electrode array for a cochlear prosthesis,; Sensors and Actuators. A Physical Transducers '97: International Conference on Solid-State Sensors and Actuators No. 9, 1998, vol. 66, Abstract.

Specialty Photonics; ClearLite Micro 980 Photonic Fiber; Specialty Single-Mode Fiber Specification Sheet; www.specialtyphotonics.com.

Dr. Rüdiger Paschotta; Encyclopedia of Laser Physics and Technology, Bend Losses; Nov. 11, 2008.

RP Photonics; Encyclopedia of Laser Physics and Technology, Bend Losses; www.rp-photonics.com/bend_losses.html.

Pennwell, Laserfocusworld; Fiber Fabrication: Single-mode Fiber has very low bending loss; www. optoiq.com/index/photonics-technologies-applications.

Wikipedia, The Free Encyclopedia; Fused Quartz; http://en.wikipedia.org/wiki/Fused_quartz.

Bhatti et al; ISSCC 2006/Session 2/Biomedical Systems/ 2.3; A 32 Site 4-Channel Cochlear Electrode Array; 2006 IEEE International Solid-State Circuits Conference; University of Michigan, Ann Arbor, MI.

(56) References Cited

OTHER PUBLICATIONS

Wang et al; An Integrated Position-Sensing System for a Mems-Based Cochlear Implant; Engineering Research Center for Wireless Integrated MicroSystems; Department of Electrical Engineering and Computer Science, University of Michigan; 2009.

Wang et al; A Hybrid Electrode Array with Built-In Position Sensors for an Implantable MEMS-Based Cochlear Prosthesis; IEEE Xplore; University of California Berkeley; 2009.

Chorost; Making Deaf Ears Hear with Light, A laser-based approach could make cochlear implants, which currently use electrical signals, more effective; www.technologyreview.com; Aug. 10, 2007.

Adunka et al; Monitoring of Cochlear Function During Cochlear Implantation; Laryngoscope 116: Jun. 2008, 1017-1255.

Polymicro Technologies; Mechanical Stress and Fiber Strength; www.polymicro.com/catalog/2_25.html.

Technica S.A.; Fiber Bragg Grating Sensor; www.technicasa.com.

Wise et al; High-Density Cochlear Implants with Position sensing and control; www.elsevier.com/locate/heares; Hearing Research 242 (2008) 22-30.

Wise et al; Wireless Implantable Microsystems: High-Density Electronic Interfaces to the Nervous System; Proceedings of the IEEE, vol. 92, No. 1, Jan. 2004.

REFDOC.FR; A flexible micromachined electrode array for a cochlear prosthesis; http://cat.inist.fr/? aModele=afficheN& cpsidt=2254424.

http://www.micronoptics.com/SENSORS_PRODUCTS.

Schurzig et al., "A Force Sensing Automated Insertion Tool for Cochlear Electrode implantation," 2010 IEEE International Conference on Robotics and Automation.

U.S. Appl. No. 61/384,934, filed Sep. 21, 2010, Titled: Optical Sensing System for Cochlear Implant Surgery.

U.S. Appl. No. 61/042,104, filed Apr. 3, 2008, Titled: Robot-Assisted Insertion of Steerable Electrode Arrays.

* cited by examiner

COCHLEAR ELECTRODE INSERTION

RELATED APPLICATIONS

The present application claims priority under 35 U.S.C. §119(e) of a previously filed U.S. provisional patent application, No. 61/110,463, filed Oct. 31, 2008 and entitled "Automated Cochlear Electrode Insertion," which application is hereby incorporated by reference in its entirety.

BACKGROUND

In human hearing, hair cells in the cochlea respond to sound waves and produce corresponding auditory nerve impulses. These nerve impulses are then conducted to the brain and perceived as sound.

When the hair cells are severely damaged or missing, one method of restoring hearing is a cochlear implant. The cochlear implant includes an electrode that is inserted into the cochlea and directly stimulates the auditory nerves using an electrical current. This bypasses the defective hair cells and restores perception of sound to the patient.

The insertion of the electrode into the cochlea is typically performed by creating an opening in the cochlea and then inserting the electrode through the opening and into the cochlea. This insertion, when performed manually, can generate forces that are large enough to damage the sensitive tissues within the cochlea. This damage can further reduce any residual hearing capability of the patient.

If hearing can be preserved, many advantages are afforded to the patient such as 1) the possibility of combined acoustic-electric hearing for better hearing in noise and music enjoyment and 2) the preservation of sensory structures that produce homeostatic levels of various growth factors that help to support spiral ganglion cell survival.

In order to increase the probability of hearing preservation in the face of electrode insertion trauma the forces exerted during insertion should, at a minimum, not exceed the mechanical limits of the tissue residing within the inner ear. It should be pointed out that the structures responsible for hearing transduction can be irreversibly damaged by forces that are below the threshold of tactile detection during manual insertion. Therefore, in order to accomplish reliable atraumatic insertions of a cochlear implant arrays, new methods must be employed that enable the management of forces that are below human detection.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

Hearing loss, which may be due to many different causes, is generally of two types: conductive and sensorineural. Conductive hearing loss typically occurs where the normal mechanical pathways for sound to reach the hair cells in the cochlea are impeded, for example, from damage to the ossicles. Conductive hearing loss may often be helped by using conventional hearing aids that amplify sounds so that acoustic information can reach the cochlea and the hair cells. Some types of conductive hearing loss are also treatable by surgical procedures.

Many people who are profoundly deaf, however, have sensorineural hearing loss. This type of hearing loss can arise from the absence or the destruction of the hair cells in the cochlea, which then no longer transduce acoustic signals into auditory nerve impulses. Individuals with complete sensorineural hearing loss are unable to derive any benefit from conventional hearing aid systems no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural deafness, cochlear implant systems or cochlear prostheses have been developed that can bypass the hair cells located in the vicinity of the radially outer wall of the cochlea by presenting electrical stimulation directly to the auditory nerve fibers. This leads to the perception of sound in the brain and provides at least partial restoration of hearing function. Thus, most of these cochlear prosthesis systems treat sensorineural deficit by stimulating the ganglion cells in the cochlea directly using an implanted electrode or lead that has an electrode array. Thus, a cochlear prosthesis operates by directly stimulating the auditory nerve cells, bypassing the defective cochlear hair cells that normally transduce acoustic energy into electrical activity to the connected auditory nerve cells. The present specification relates to neural stimulators and, particularly, to cochlear implant systems that include electrode arrays for stimulation of a patient's cochlea. In a typical cochlear implant, an array of electrode contacts are placed along one side of an elongate carrier or lead so that when the array is implanted within one of the cochlear ducts, such as the scala tympani, the electrode contacts are positioned in close proximity to the cells that are to be stimulated. This allows such cells to be stimulated with minimal power consumption.

Prior to stimulating the nerve cells, the electronic circuitry and the electrode array of the cochlear prosthesis separate acoustic signal into a number of parallel channels of information, each representing a narrow band of frequencies within the perceived audio spectrum. Ideally, each channel of information should be conveyed selectively to a subset of auditory nerve cells that normally transmit information about that frequency band to the brain. Those nerve cells are arranged in an orderly tonotopic sequence, from the highest frequencies at the basal end of the cochlear spiral to progressively lower frequencies towards the apex.

To maximize the benefit of the surgery for the patient, it is important to preserve the residual hearing of the patient and to maximize the long-term effectiveness of the cochlear implant. As the cochlear lead is inserted through the tissues in the head and into the cochlea, there can be mechanical damage to the surrounding tissues, subsequent inflammation, and possibly damage to the delicate structures within the cochlea. Additionally, mechanical damage to the interior of the cochlea can result in tissue growth around the cochlear implant and eventual ossification. This tissue growth can act as a barrier between the electrodes of the cochlear implant and the target nerves. This can lead to a degradation of the performance of the cochlear implant over time.

Electrical stimulation of predetermined locations within the cochlea of the human ear through an intracochlear electrode array is described, e.g., in U.S. Pat. No. 4,400,590 (the "'590 patent"), which is incorporated herein by reference. The electrode array shown in the '590 patent comprises a plurality of exposed electrode pairs spaced along and imbedded in a resilient curved base for implantation in accordance with a method of surgical implantation, e.g., as described in U.S. Pat. No. 3,751,605, which is incorporated herein by reference. The system described in the '590 patent receives audio signals, i.e., sound waves, at a signal processor (or speech processor) located outside the body of a hearing-impaired patient. The speech processor converts the received audio signals into modulated radio frequency (RF) data signals that are transmitted through the patient's skin and then by a cable connection to an implanted multi-channel intracochlear electrode array. The modulated RF signals are demodulated into analog signals and are applied to selected contacts of the plurality of exposed electrode pairs in the intracochlear electrode so as to electrically stimulate predetermined locations of the auditory nerve within the cochlea.

U.S. Pat. No. 5,938,691, incorporated herein by reference, shows an improved multi-channel cochlear stimulation system employing an implanted cochlear stimulator (ICS) and an externally wearable speech processor (SP). The speech processor employs a headpiece that is placed adjacent to the ear of the patient, which receives audio signals and transmits the audio signals back to the speech processor. The speech processor receives and processes the audio signals and generates data indicative of the audio signals for transcutaneous transmission to the implantable cochlear stimulator. The implantable cochlear stimulator receives the transmission from the speech processor and applies stimulation signals to a plurality of cochlea stimulating channels, each having a pair of electrodes in an electrode array associated therewith. Each of the cochlea stimulating channels uses a capacitor to couple the electrodes of the electrode array.

Over the past several years, a consensus has generally emerged that the scala tympani, one of the three parallel ducts that make up the spiral-shaped cochlea, provides the best location for implantation of an electrode array used as part of a cochlear prosthesis. The electrode array to be implanted in the scala tympani typically consists of a thin, elongated, flexible carrier containing several longitudinally disposed and separately connected stimulating electrode contacts, conventionally numbering about 6 to 30. Such an electrode array is pushed into the scala tympani duct in the cochlea to a depth of about 20-30 mm via a cochleostomy or via a surgical opening made in the round window at the basal end of the duct.

In use, the cochlear electrode array delivers electrical current into the fluids and tissues immediately surrounding the individual electrode contacts to create transient potential gradients that, if sufficiently strong, cause the nearby auditory nerve fibers to generate action potentials. The auditory nerve fibers branch from cell bodies located in the spiral ganglion, which lies in the modiolus, adjacent to the inside wall of the scala tympani. The density of electrical current flowing through volume conductors such as tissues and fluids tends to be highest near the electrode contact that is the source of such current. Consequently, stimulation at one contact site tends to selectively activate those spiral ganglion cells and their auditory nerve fibers that are closest to that contact site. Conventionally, after implant, the electrode array consisting of electrode contacts should hug the modiolar wall (or inside wall of the scala tympani), without causing undue pressure. When the electrode side of the array is positioned closest to the modiolar wall, the electrode contacts are on the medial side of the lead.

Other patents relevant to the subject matter of cochlear stimulation leads are: U.S. Pat. Nos. 6,125,302; 6,070,105; 6,038,484; 6,144,883; and 6,119,044, which are all herein incorporated by reference. Other improved features of cochlear implant systems are taught, e.g., in U.S. Pat. Nos. 6,129,753; 5,626,629; 6,067,474; 6,157,861; 6,249,704; and 6,289,247, each of which is incorporated herein by reference.

U.S. Pat. No. 5,784,542, incorporated herein by reference, describes a six degree of freedom tele-operated robot system for robot-assisted microsurgery. A remote master robot is manipulated by a surgeon and the sensed forces and motion are transferred to the slave robot that performs the microsurgery. Force feedback is provided to the master robot by the slave robot. U.S. Patent Application Pub. No. 20070225787, incorporated herein by reference, discloses an insertion module that is used to translate surgeon inputs into motion and sense forces that insert the cochlear electrode into the cochlea. These sensed forces can be displayed to guide the surgeon during the operation.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example" or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

Throughout the specification, a cochlear implant is used as just one example of an implanted medical device. The principles discussed in the present specification can be applied to a wide range of implanted medical devices. Further, as used in the present specification and the appended claims, the term "automated" is meant to be understood broadly as completely automated, semi-automated or manually controlled based on sensor feedback, or combinations thereof.

Figure 1:
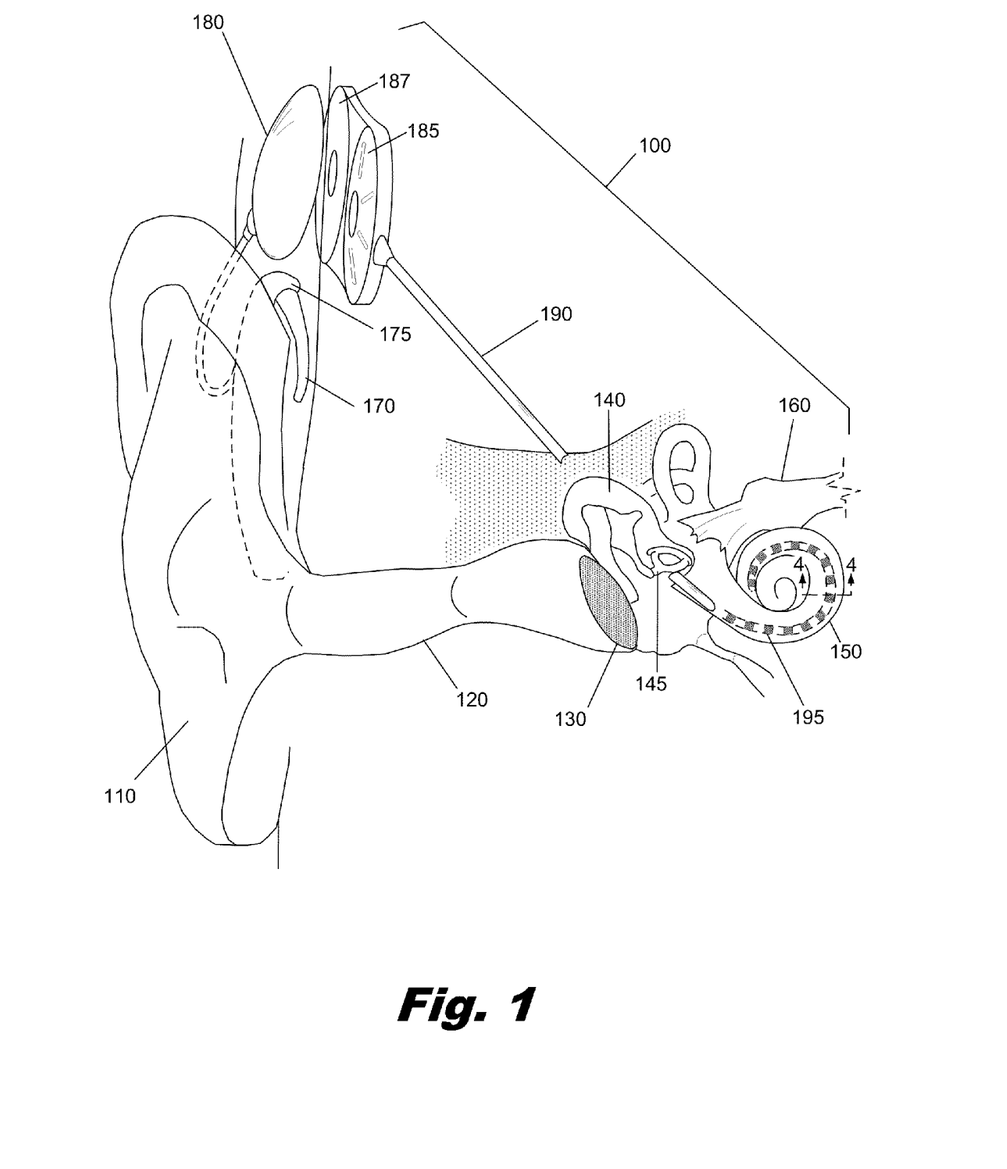
FIG. 1 is an illustrative diagram showing an illustrative cochlear implant system, according to one embodiment of principles described herein.

FIG. 1 is a diagram showing one illustrative embodiment of a cochlear implant (100) surgically placed within the patient's auditory system. Ordinarily, sound enters the outer ear (110) and is directed into the auditory canal (120) where the sound wave vibrates the tympanic membrane (130). The motion of the tympanic membrane is amplified and transmitted through the ossicular chain (140) which consists of three bones in the middle ear. The third of the ossicles, or stirrup, (145) contacts the outer surface of the cochlea (150) and causes movement of the fluid within the cochlea (150). Cochlear hair cells respond to the fluid-borne vibration in the cochlea (150) and trigger neural electrical signals that are conducted from the cochlea (150) to the auditory cortex by the auditory nerve (160).

As indicated above, the cochlear implant (100) is a surgically implanted electronic device that provides a sense of sound to a person who is profoundly deaf or severely hard of hearing. As also noted above, in many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

Unlike hearing aids, the cochlear implant (100) does not amplify sound, but works by directly stimulating any functioning auditory nerve cells inside the cochlea (150) with electrical impulses. Consequently, providing a cochlear prosthesis typically involves the implantation of electrodes into the cochlea. The cochlear prosthesis operates by direct electrical stimulation of the auditory nerve cells, bypassing the defective cochlear hair cells that normally traduce acoustic energy into electrical energy.

External components of the cochlear implant include a microphone (170), sound processor (175), and transmitter (180). The microphone (170) picks up sound from the environment and converts it into electrical impulses. The sound processor (175) selectively filters and manipulates the electrical impulses and sends the processed electrical signals through a cable to the transmitter (180). The transmitter (180) receives the processed electrical signals from the processor (175) and transmits them to the receiver (185) by electromagnetic, radio frequencies, optical communication, and/or other wireless communication technology.

The internal components of the cochlear implant may include an antenna (187) and an internal processor (185). The antenna (187) and internal processor (185) are secured beneath the user's skin, typically above and behind the external ear (110). The internal processor (185) includes electronic circuitry housed in a hermetically sealed enclosure. This electronic circuitry is connected, via a hermetically sealed feedthrough, to the antenna (187). The antenna (187) receives power and signals from the transmitter (180) via electromagnetic induction, radio frequency signals, optical communication, and/or other wireless communication. In some cochlear implants, the transmitter (180) is held in place by magnetic interaction with the underlying antenna (187). The internal processor (185) processes the received signals and sends modified signals through the hermetic feedthrough to cochlear lead (190) and electrode array (195). The electrode array (195) is wound through the cochlea (150) and provides direct electrical stimulation to the auditory nerve (160) inside the cochlea (150) which bypasses the normal mechanics of hearing and results in synaptic excitation of the auditory nerve (160).

The implant works by using the tonotopic organization of the basilar membrane of the inner ear. The tonotopic organization, also referred to as "frequency- to-place" mapping, is the way the ear differentiates between sounds of different frequencies. In a normal ear, sound vibrations in the air are converted into resonant vibrations of the liquid within the cochlea. High-frequency sounds do not pass very far through the liquid and the structures of the cochlea that contain the liquid. Low-frequency sounds pass farther down the cochlear channels. Consequently, the nerve cells at the basal end of the cochlear spiral sense higher frequencies, while progressively lower frequencies are sensed at different portions of the cochlear spiral moving towards the apex. The movement of hair cells located all along the basilar membrane stimulates the surrounding nerve cells, which conduct electrical impulses to the brain. The brain is able to interpret the nerve activity to determine which area of the basilar membrane is resonating and, therefore, what sound frequencies are being heard.

For individuals with sensorineural hearing loss, hair cells are often fewer in number and/or damaged. The cochlear implant bypasses the hair cells and stimulates the cochlear nerves directly using electrical impulses. The cochlear implant stimulates different portions of the cochlea (150) according to the sound detected by the microphone (170), just as a normal functioning ear would experience stimulation at different portions of the cochlea depending on the frequency of sound vibrating the liquid within the cochlea (150). This allows the brain to interpret the frequency of the sound as if the hair cells of the basilar membrane were functioning properly.

Figure 2:
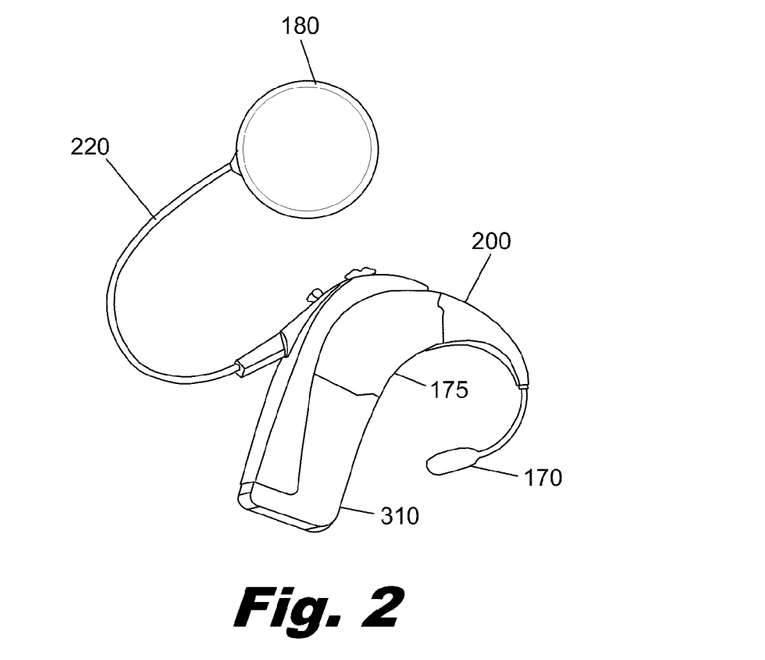
FIG. 2 is an illustrative diagram showing the external components of an illustrative cochlear implant system, according to one embodiment of principles described herein.

FIG. 2 shows one illustrative embodiment of the external components of the cochlear implant. The microphone (170) is attached to the ear hook (200). The ear hook (200) secures the external components behind the outer ear. The microphone (170) senses environmental sounds and converts those sounds into electrical impulses. The processor (175) filters and manipulates the electrical impulses it receives from the microphone (170) and transmits processed electrical sound signals along the external cable (220) to the transmitter (180). The processor (175), microphone (170), and transmitter (180) are powered by a battery (310).

Figure 3:
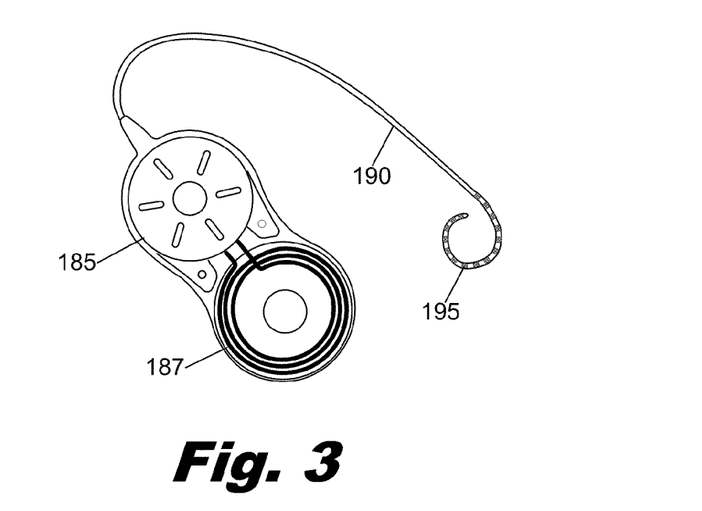
FIG. 3 is an illustrative diagram showing the implanted components of an illustrative cochlear implant system, according to one embodiment of principles described herein.

FIG. 3 shows one illustrative embodiment of the internal components of the cochlear implant device. As described above, the antenna (187) is connected to the internal processor (185). According to one embodiment, the antenna (187) is a coiled wire or wires that are encapsulated by a silicone overcoat. A cavity within the center portion of the antenna (187) is adapted to receive a magnet, which provides the magnetic force required to hold the external transmitter (180) in place over the antenna (187). The internal processor (185) is electrically connected to antenna (187) and receives signals and power via the antenna (187). The internal processor (185) is connected to the cochlear lead (190) which terminates in a flexible end that contains the electrode array (195). The electrode array (195) consists of a plurality of individual electrodes contacts made from platinum or a similarly highly conductive material. These electrodes and associated wires are supported and connected by a flexible and durable biocompatible material, typically silicone rubber.

Figure 4A:
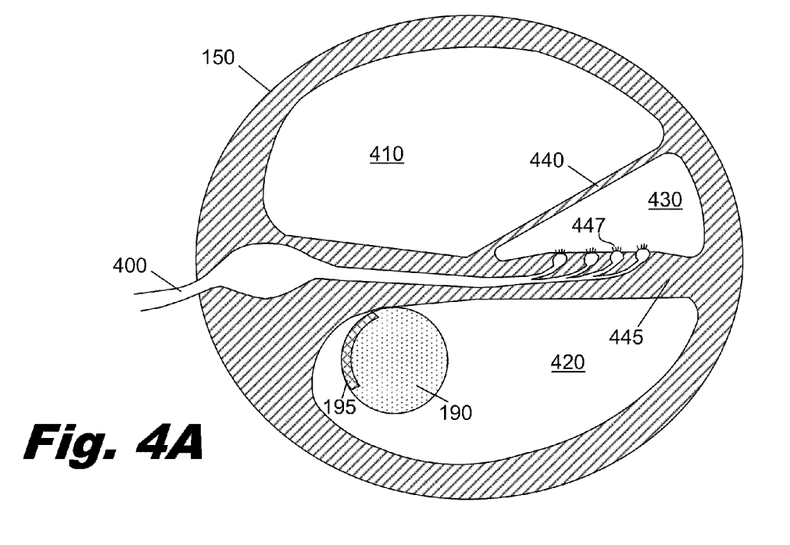
FIGS. 4A and 4B are illustrative cross-sectional diagrams of the cochlea showing the internal structure of the cochlea and insertion locations for an intracochlear lead, according to one embodiment of principles described herein.
Figure 4B:
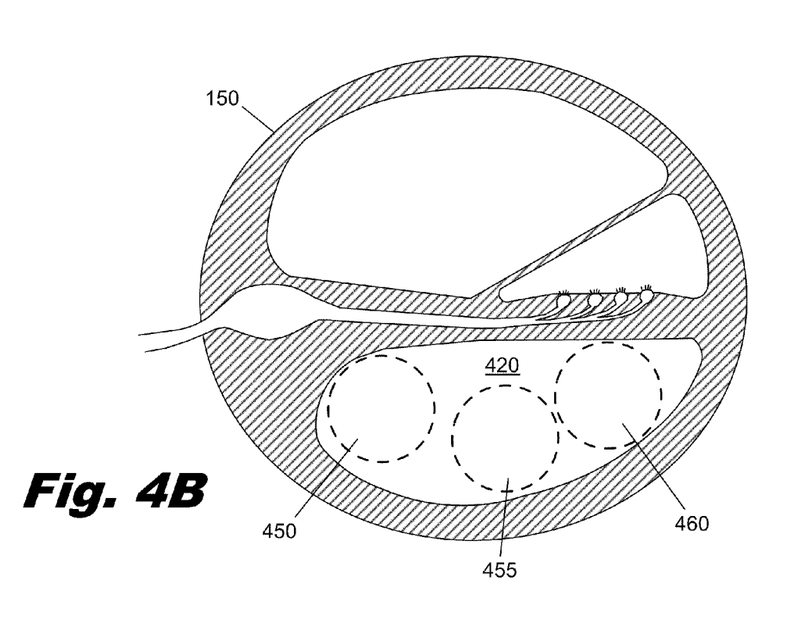

FIGS. 4A and 4B are cross sectional diagrams of the cochlea (150) taken along line 4-4 of FIG. 1. The walls of the hollow cochlea (150) are made of bone, with a thin, delicate lining of epithelial tissue. The primary structure of the cochlea is a hollow tube that is helically coiled, similar to a snail shell. The coiled tube is divided into three fluid-filled spaces (scalae), the scala vestibuli (410), the scala tympani (420), and the scala media (430). Reissner's membrane, or the vestibular membrane, (440) separates the scala media (430) from the scala vestibuli (410), and the basilar membrane (445) separates the scala tympani (420) from the scala media (430). The scala vestibuli (410) joins the scala tympani (420) at the apex of the cochlea.

The cochlea (150) is filled with a watery liquid, which moves in response to the vibrations coming from the middle ear via the stirrup (145, FIG. 1). As the fluid moves, thousands of "hair cells" (447) in a normal, functioning cochlea are set in motion and convert that motion to electrical signals that are communicated via neurotransmitters to many thousands of nerve cells (400). These primary auditory neurons (400) transform the signals into electrical impulses known as action potentials, which travel along the auditory nerve to structures in the brainstem for further processing. The terminal end of the cochlear lead (190, FIG. 1) is inserted into the scala tympani with the electrode array (195, FIG. 1) being positioned in close proximity to the nerve (400).

FIG. 4B is a cross sectional diagram of the cochlea (150) showing various positions of cochlear lead (190) within the scala tympani (420). The cochlear lead (190) may be in a modiolar hugging position (450), mid-modiolar position (455), or a lateral wall position (460). Each of these positions may be suitable for a cochlear lead and allow for adequate stimulation of the auditory nerve. Depending on the cochlear implant design, one position may be preferred over other positions. In this regard, the cochlear lead is preferably designed for insertion into the cochlea with the least degree of trauma to the cochlea as possible.

Figure 5:
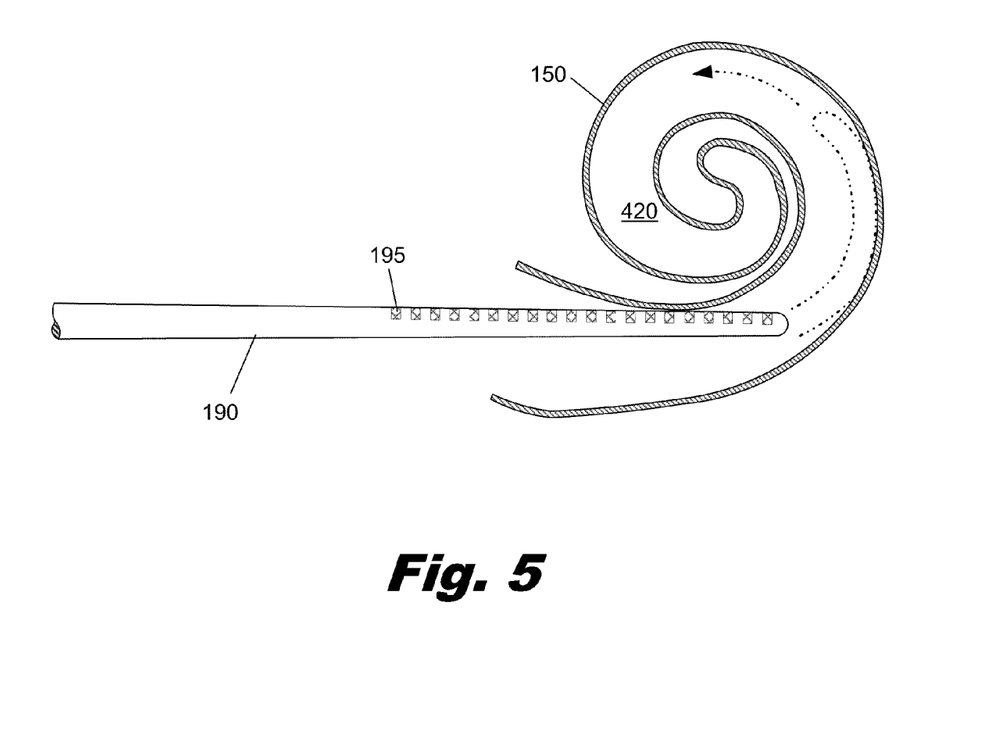
FIG. 5 is an illustrative cross-sectional diagram of the cochlea showing the electrode being inserted into the cochlea, according to one embodiment of principles described herein.

As shown in FIG. 5, the tip of the cochlear lead (190) is inserted through an incision in the cochlea (150) and pushed into the scala tympani (420) so that the entire lead conforms to the helical shape of the scala tympani. A major problem with electrode insertion is potential damage to the delicate structures within the cochlea. To insert the cochlear lead, a passageway is made through the body tissues of the head to expose the cochlea. The tip of the electrode is inserted through an opening in the cochlea. The electrode array (195) is then pushed axially into the cochlea. The force of the tip against the walls of the cochlear channel may bend the flexible tip, causing trauma to the walls of the cochlear channel. Further, additional trauma to walls of the cochlear channel may be experienced as the entire electrode array (195) is inserted, wherein other portions of the length of the electrode array (195) rub or create forces against the walls of the cochlear channel. Thus, it is important to minimize these forces during insertion of the cochlear lead (190).

When the tip is in its final position, the electrode array (195) is entirely contained within the cochlea and the individual electrodes are placed proximate the nerve cells (400, FIG. 4A). When electrical current is routed into an intracochlear electrode (195), an electric field is generated and the auditory nerve fibers (400, FIG. 4A) are selectively stimulated.

The individual electrodes within the electrode array can be used in a variety of configurations to provide electrical stimulation to the auditory nerve fibers. In a monopolar configuration, an electrical ground is provided, either internal or external to the cochlea. Each of the electrodes can then be used individually to stimulate adjacent auditory nerves. In a bipolar configuration, the electrodes are grouped in adjacent pairs, with one electrode being used as a ground and the other electrode providing active electrical stimulation. A variety of other configurations are possible, such as multipolar stimulation.

Forces that can damage tissues within the cochlea are at least an order of magnitude smaller than forces typically exerted during a manual insertion of a cochlear lead, and are very difficult to accurately sense with the human hand. Additionally, the human hand may not be capable of consistently keeping applied forces below the threshold for tissue damage. For example, accidental movement and/or tremors in the surgeon's motion can exceed the allowable force limits. In one exemplary embodiment, in order to prevent insertion damage, an insertion tool is used to insert the electrode while monitoring the applied forces. The insertion tool is sensitive enough to measure very small forces, such as sub-micronewton or millinewton levels of force and prevent application of forces over a maximum threshold. This maximum threshold may be an experimentally derived limit that is determined based on successful outcomes of past surgeries.

Figure 6:
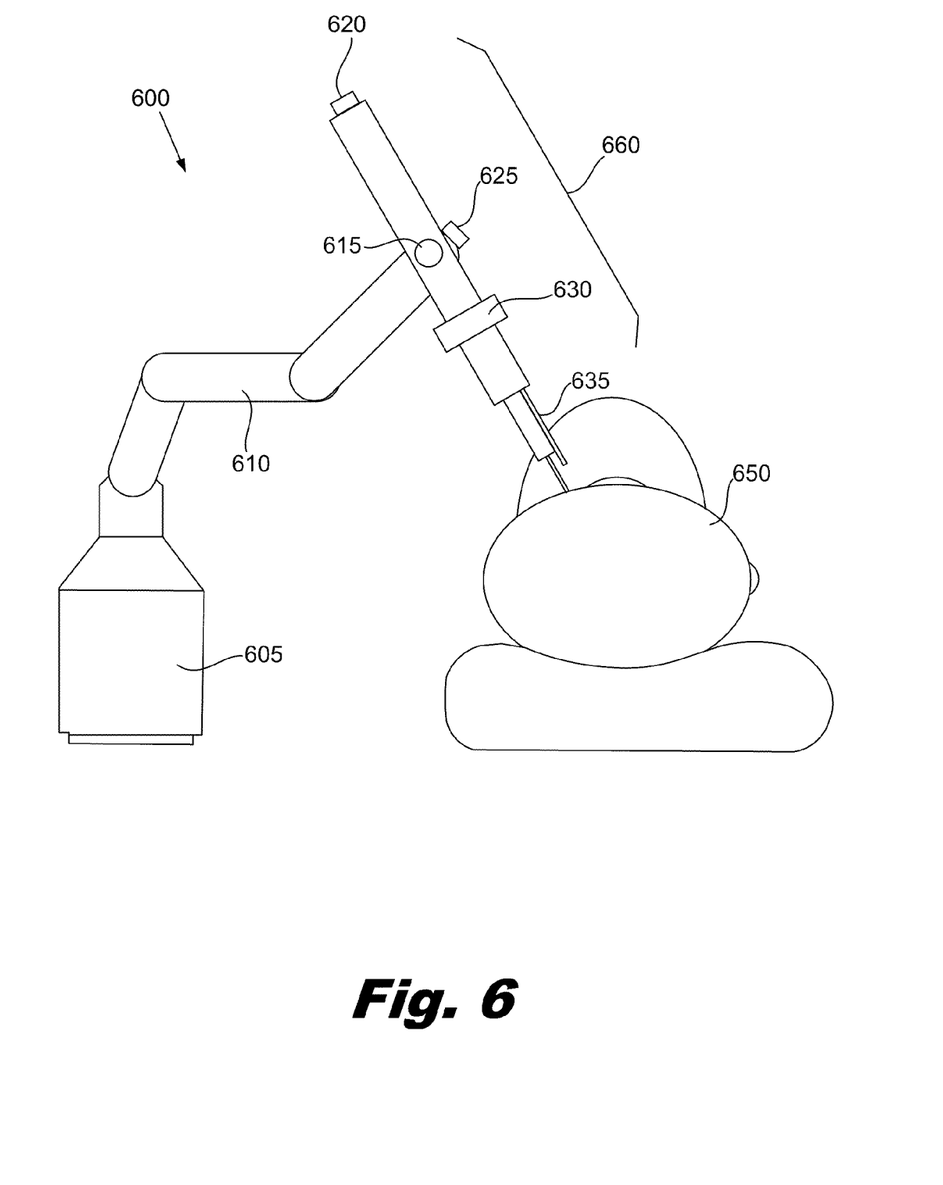
FIG. 6 shows one illustrative embodiment of an insertion tool, according to one embodiment of principles described herein.

FIG. 6 shows one illustrative embodiment of an insertion tool (600) which may be used for automated cochlear electrode insertion into a patient (650). According to one illustrative embodiment, the insertion tool (600) may be made up of a base (605), a number of articulated members (610) attached to the base, and an insertion head (660).

The insertion head (660) may include a number of micromanipulators (615, 620, 625). The micromanipulators (615, 620, 625) allow for fine adjustments to the position of the insertion head (660). For example, a first micromanipulator (615) may provide rotational positioning, a second micromanipulator (620) may provide in/out positioning, and a third micromanipulator (625) may provide left/right positioning of the insertion head (660). The micromanipulators (615, 620, 625) may be adjustable both manually and by actuators. For example, the micromanipulators (615, 620, 625) may include both an external knob for manual adjustments and an electrical stepper motor for making computer-controlled adjustments to the insertion head (660). In addition to or in place of the electrical stepper motor, an AC synchronous servomotor or a DC drive motor may be used. The motors may be coupled to the cochlear lead (190, FIGS. 1 and 5) and/or a tool coupled to the cochlear lead (190, FIGS. 1 and 5). To further assist in the approach to the cochleostomy, the insertion tool (600) could be capable of being registered with a surgical navigational system that incorporated preoperative or intraoperative imaging to assist in proper alignment.

The insertion head (660) may be configured to accept and operate standard handheld instruments or may use custom insertion instruments. For example, the insertion tool (600) could also function in the capacity of providing automated drilling of the cochleostomy by incorporating a drill tool attachment. Additionally, for navigationally assisted minimally invasive surgery that may drill directly from the skull surface to the cochleostomy, this tool would also be capable of allowing automated electrode insertion via a 1-1.5 millimeter diameter hole that is 2-10 millimeters in length. However, the length of the hole may be longer in some patients due to the distance between the skull surface and cochlea of a particular patient. Therefore, the insertion tool (600) may be configured to penetrate a greater distance.

According to one illustrative embodiment, the insertion tool (600) also includes a ring-slider (630). The ring-slider (630) controls the insertion of the cochlear lead by allowing the cochlear lead to be advanced toward or withdrawn from the body tissues. Additionally, the ring-slider (630) may allow the cochlear lead to be rotated clockwise or counterclockwise about the longitudinal axis of the insertion head (660). The ring-slider (630) is only one illustrative embodiment of mechanisms that could be used to manipulate the cochlear lead. Other actuators could be used. For example, pneumatic, hydraulic, piezoelectric, electromechanical, magnetic, or other actuators could be used. These actuators could be arranged in a variety of ways including configurations that allow for additional degrees of freedom. For cochlear leads with active controls allowing for additional feedback in connection with the position of the cochlear lead within the cochlea, the automated insertion tool may also have output capability to provide steering signals to the lead.

The insertion head (660) may also include an imaging device (635), which may be a fiber optic or endoscopic imager. For example, the imaging device (635) may include a rigid or flexible tube, a light delivery system to illuminate the tissues of interest, and an optical system, which transmits an image of the tissues to the outside observer. The optical system may convey the image directly to an outside observer or detector. Additionally or alternatively, the optical system may directly convert the image to electronic signals, which are then transmitted through endoscope. The imaging device (635) may be separate from the insertion mechanism or may be combined with the insertion mechanism.

The insertion tool (600) is equipped with force sensors that measure the insertion force. This real time force data can be displayed for inspection by the surgeon, serve as inputs to the automated insertion algorithm running on a control system, and/or provide feedback for haptic control devices. A haptic control device may be any control device that is related to or based on the sense of touch to control another element or device. Force sensors may be provided that are capable of detecting forces in the in/out translational, pitch/yaw pivot, and/or the left/right directions of rotational motion. The sensors may be based on piezoresistance, piezoelectric sensory, capacitance, electrostatic sensory, optics, or acoustics. Further, the present system may incorporate micro electromechanical systems (MEMS), nano-load cell bridges, strain gauges, or other technologies used to measure sub-micronewton forces. In addition to force sensing capability within the insertion tool (600), the system may have inputs that can be used to relay information from sensors within the electrode, which provide additional feedback. Alternatively, sensors on the electrode may be the sole source of feedback. In another exemplary embodiment, sensors may be placed juxtaposition to the biological tissues upon which the insertion tool (600) is operating. This force data may be encrypted prior to being reported back to the controller for storage, analysis, or dissemination.

Figure 7:
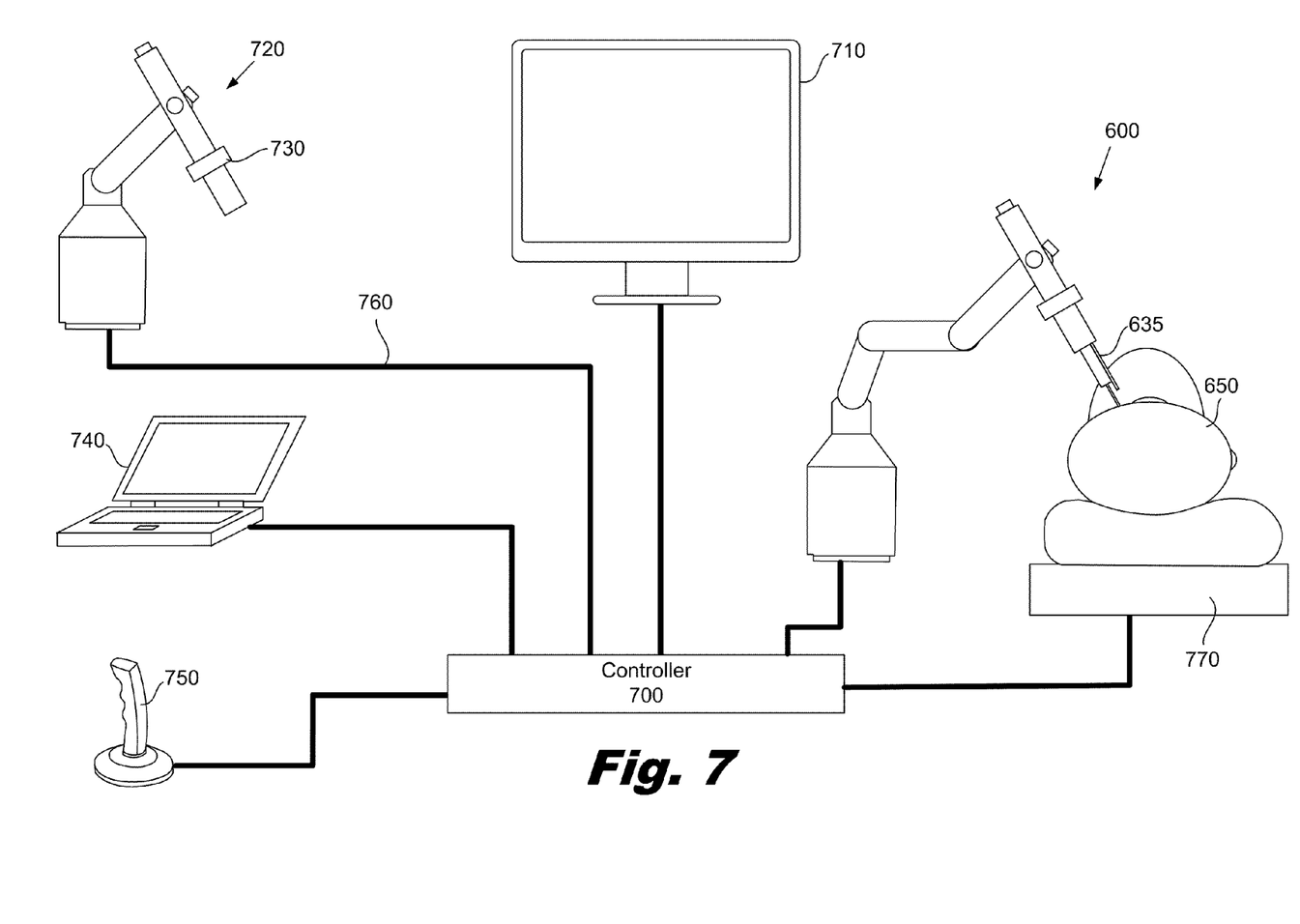
FIG. 7 is diagram of an illustrative system for automated insertion of a cochlear electrode, according to one embodiment of principles described herein.

FIG. 7 is diagram of an illustrative system for automated insertion of a cochlear electrode. According to one illustrative embodiment, a patient (650) is positioned and stabilized in preparation for the surgery. The patient may be stabilized using a variety of techniques including specialized pillows, pads, halos, stereotactic frames, or other suitable mechanisms. According to one embodiment, the patient (650) may be lying on a bed (770) that is adjustable in one or more directions. For example, the bed (770) may have an adjustable height. In an alternative embodiment, the automated insertion tool (600), while being primarily supported by a platform or table, is attached directly to the patient's head via a stereotactic frame. This provides a stable connection between the automated insertion tool (600) and operating location.

The automated insertion tool (600) is positioned and prepared for the surgery. The appropriate instruments are attached to the insertion head and the cochlear lead is connected to the instruments. As discussed previously, the automated insertion tool may have a number of micro-adjusters that allow for precise positioning of the automated insertion tool (600) with respect to the patient's head.

The automated insertion tool (600) is attached to a controller (700). In the illustrative embodiment shown in FIG. 7, the controller (700) is shown as a freestanding unit. However, the controller could be integrated into any one of a number of other components, including, but not limited to, a personal computer, a distributed computing network, the automated insertion tool itself, or a remote computer. Additionally, the controller (700) could use a variety of algorithms that analyze previous surgical data. By way of example and not limitation, these algorithms could include genetic algorithm, or other learning techniques to assist in providing optimal insertion trajectories based on previous insertion data. The system could be "pre-loaded" with the experience of thousands of insertions to aid predictive capabilities and efficiency. Additionally or alternatively, insertion "learning" data could be pulled/shared across various surgery centers and the latest learning data downloaded for local use. This insertion data could include various metadata that allow the insertion data to be categorized and used appropriately to control lead insertion. For example, there may be different insertion trajectories and optimal rotational timing between left and right cochlea.

A monitor (710) is also connected to the controller (700). The monitor (710) may display information relating to the surgery including display of images from the imaging device (635), a graph of the force applied as a function of time, a graph of force applied as a function of insertion depth, a display of estimated angular insertion depth, radiological imaging data, and other information. The monitor (710) may be local to the operation or in a remote location.

Other feedback devices could also be used. By way of example and not limitation, sound feedback could be provided which audibly indicates the applied force by using pitch or amplitude of the sound. For example, higher forces could be indicated by using higher pitches and/or higher amplitudes. The approach of forces to a predetermined limit could be indicated by an intermittent warning tone that, for example, increased in frequency as the limit is approached.

In the event that human intervention is required, a number of devices can be used to input the desired information. For example, a haptic controller (720) could be used by a surgeon to take corrective action. The haptic controller (720) could have a variety of designs. According to one illustrative embodiment, the haptic controller (720) could be substantially identical to the insertion tool (600). The feedback sensors within the haptic controller (720) could sense the manually applied pressure on the haptic ring-slider (730) in substantially the same manner that feedback sensors on the insertion tool (600) sense the applied pressure as the cochlear lead is inserted. The haptic controller (720) would allow the same degrees of freedom as the insertion tool (600) (e.g. left/right rotational, pitch/yaw pivot, and in/out translational motion). The force signal from the insertion tool (600) could be used to provide haptic feedback to the surgeon while limiting the maximal forces exerted in both the in/out and rotational directions. This force feedback would allow the operator to "feel" an amplified version of forces detected by the electrode. The sensitivity and force amplification functions may be adjusted by the surgeon to give the best resistance as a function of force applied by the insertion tool (600). As will be explained in more detail below, a force profile may be provided that may assist the surgeon in determining the best level of sensitivity and force amplification. This, in turn, will help ensure that a path of least resistance for the insertion of the cochlear electrode is followed as closely as possible.

Various haptic interfaces for medical simulation prove especially useful for training of minimally invasive procedures and for performing remote surgery using teleoperators.

For example, an expert surgeon may work from a central workstation, performing operations in various locations, with machine setup and patient preparation performed by local nursing staff. Rather than traveling to an operating room, the surgeon instead becomes a telepresence. A particular advantage of this type of work is that the surgeon can perform many more operations of a similar type, and with less fatigue. It is well documented that a surgeon who performs more procedures of a given kind will have statistically better outcomes for his patients.

According to one embodiment, the haptic ring-slider (730) would provide the surgeon with haptic feedback, which simulates the actual resistance to the insertion of the cochlear lead by the insertion tool (600). However, as mentioned above, the levels of allowable force are so low that the human senses cannot reliably sense and respond to the actual force levels. Consequently, the haptic feedback provided by the haptic controller (720) via the haptic ring-slider (730) may be amplified to allow the surgeon to more comfortably and accurately control the motion of the insertion tool (600).

Other devices, such as computer (740) and joystick (750) may, additionally or alternatively, be used to remotely control the motion of the insertion tool (600). The computer (740) could be used to select one of a plurality of automated approaches that best fits the situation. For example, the computer (740) may access a library of trajectory and force profiles of successful surgical insertions of cochlear electrode arrays. In situations where the automated insertion tool (600) is unable to proceed within the operational parameters, the surgeon could search the library for similar situations by matching the current insertion profile and/or radiographic data to determine how similar problems have been successfully solved in the past. The surgeon could then instruct the computer (740) to send operational commands to the automated insertion tool (600) which closely match the corresponding past solution.

A variety of other suitable controlling devices could be used. Additionally, the configurations shown are only one illustrative example of an automated insertion system. By way of example and not limitation, any or all of the illustrative auxiliary components (710, 720, 740, 750) could be local or remote. The connections (760) between the controller and other components could be wired or wireless. In some embodiments, a mixture of wired and wireless connections may be made within the system. For example, the haptic controller may have a wireless connection, thereby allowing the surgeon to place the haptic controller in the most convenient location within a surgery bay. In other embodiments, a connection between the controller (700) and other components may pass through a variety of different connection types. For example, when the surgeon is performing a telesurgery, the controlling computer may be remote from the insertion tool. The controlling computer or other device may have a wireless connection to a hub, which is then wired to a network that is in communication with the insertion tool (600) or controller (700).

The controller (700) may make a number of modifications to the input provided by the surgeon. In addition to scaling down the forces applied by the surgeon using the haptic controller (720), the controller may also remove artifacts from the input, such as tremors or accidental motions.

Figure 8:
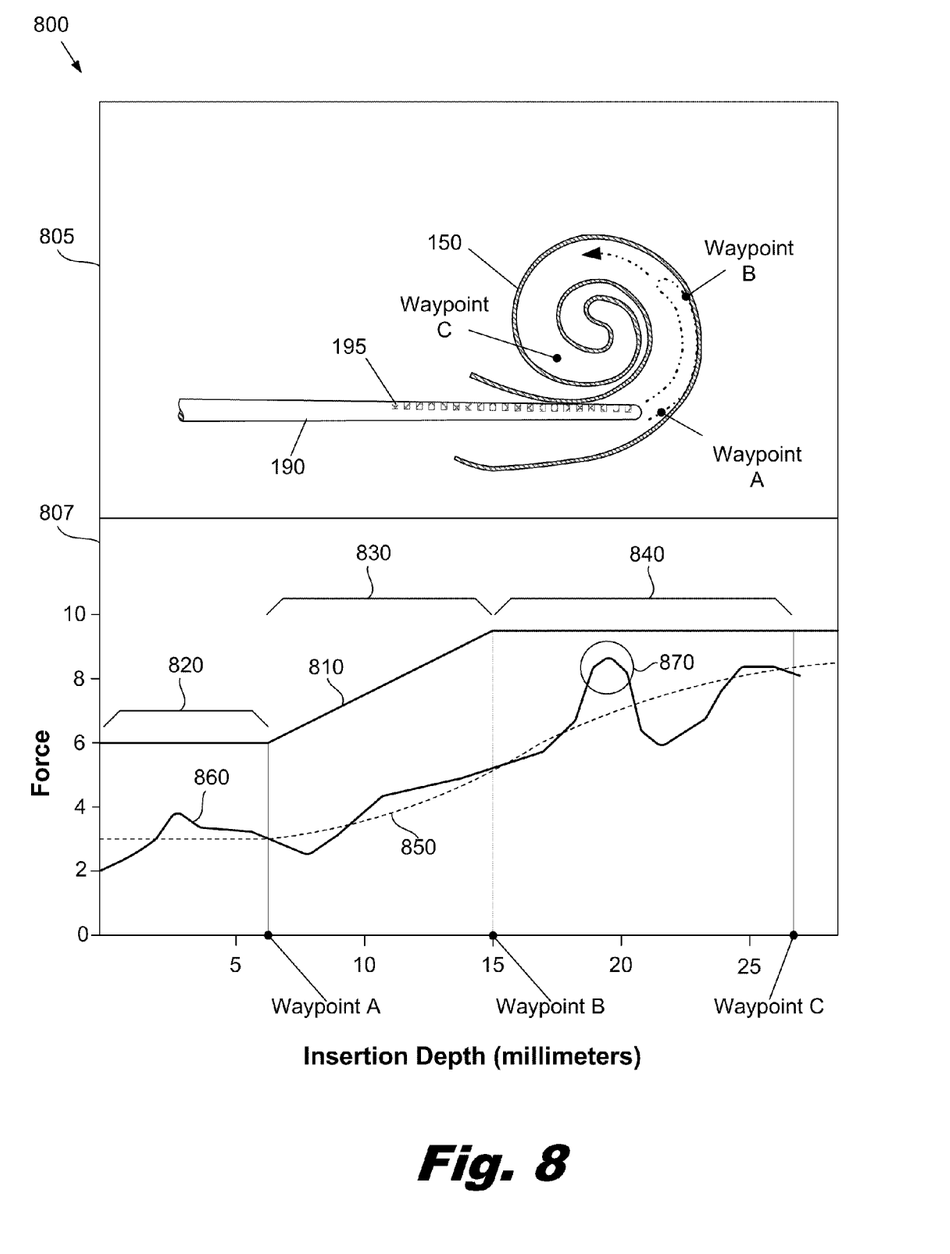
FIG. 8 is an illustrative screenshot of a display that provides information about an ongoing or past electrode insertion procedure, according to one embodiment of principles described herein.

FIG. 8 is an illustrative screenshot of a display (800) which provides information about an ongoing or past electrode insertion procedure. The screenshot (800) includes an upper window (805) showing the current position of the cochlear electrode (190) within the cochlea and a lower window (807) showing a force/insertion depth graph.

The current position of the cochlear electrode (190) within the cochlea (150) could be determined in a number of ways. In one illustrative embodiment, a real time image of the electrode moving within the patient's cochlea is displayed during the insertion. This real time image could be generated in a variety of ways, including fluoroscopy. This approach could have the advantages of immediately detecting unforeseeable events such as the electrode folding over on itself or rupture of the cochlear wall.

Additionally or alternatively, a single X-ray, magnetic resonance imaging (MRI), intermittent fluoroscopy, ultrasound, or CAT scan image of the patient's cochlea could be taken without continuously generating X-rays throughout the procedure and subjecting the patient to a high level of ionizing radiation than may be desirable. Further, these imaging techniques reduce or eliminate obstruction to the surgery location and otherwise do not interfere with the surgical procedure. The positional data from the insertion tool could be used to estimate the position of the electrode array within the cochlea. This simulated position could then be displayed as an overlay that is placed on top of the radiographic image. In another embodiment, an "average" cochlea could be displayed. For example, given the patient's diagnostic imaging, case history, and diagnosis, a cochlear model could be selected from a library. This cochlear model would then be checked to determine if it was a good match to the patient's actual cochlear geometry.

In other embodiments, a three dimensional model of the patient's cochlea could be generated using a variety of imaging techniques, including stereotactic imaging which produces a real-time image of the patient's cochlea. This three dimensional model could then be used for practice insertions or for visual feedback during the actual insertion.

A number of waypoints (waypoints A, B, and C) could be placed on the image to mark important transitions during the cochlear insertion. By way of example and not limitation, waypoint A could be placed in a location corresponding to the initial contact of the tip of the electrode (190) with the cochlear wall. Waypoint B could be placed at the point at which the tip of the electrode (190) would be expected to leave the wall. Waypoint: C could be placed at the final position of the electrode tip when the electrode is correctly and fully inserted into the cochlea.

The lower window (807) illustrates force in micronewtons as a function of insertion depth. There are three force curves represented within the lower window (807). The first curve is a maximum allowable force profile (810). For example, the maximum allowable force profile (810) may preclude the application of forces above 10 micronewtons. The illustrated maximum allowable force profile (810) is a piecewise curve, which represents the maximum force that is allowed before the insertion is stopped, and mitigating action is taken. The maximum allowable force profile (810) is divided into 3 sections: a first section (820) which represents the insertion of the electrode tip into the cochlea to waypoint A; a second section (830) which represents a region of increasing allowable force as the tip continues around the first curve of the cochlea to waypoint B; and a final section (840) which represents the allowable insertion force from waypoint B to the final position of the cochlear tip at waypoint C.

The maximum force profile (810) may be generated in a variety of ways. For example, a number of electrode insertions can be monitored and the applied forces recorded. The success of the individual operations in minimizing the force can be estimated by comparing the preoperative and postoperative residual hearing capability of the patient. The difference between the preoperative and postoperative residual hearing capability represents the hearing loss that resulted from the surgery. The hearing loss can be segmented into various frequency categories. Using a tonotopic mapping, the hearing loss in various frequencies can be mapped to specific locations within the cochlea. The recorded force and insertion data from the operation could then be used to determine which forces may have caused damage to cochlear tissues in locations where the hearing loss occurred.

Damage to a human cochlea due to insertion of a cochlear electrode array could also be directly determined by performing a number of insertions on cadaver specimens. The postoperative cochlea could then be dissected to directly examine and quantify the damage to the intracochlear tissues.

Additionally, the accumulated data could be analyzed to determine minimum force trajectories for inserting cochlear electrode arrays. These minimum force trajectories may be generated using a software learning algorithm. In some circumstances, the minimum force trajectory may comprise a number of three-dimensional waypoints. In other embodiments, the minimum force trajectory may include describe a multidimensional trajectory of the cochlear lead that is expected to require minimum insertion force, and, more specifically, a complete three-dimensional position of the electrode coupled to applied forces. Selecting a minimum force trajectory is one of the operating parameters that could be selected prior to beginning the operation. While the minimum force trajectory may form the fundamental basis for the motion and forces applied to the electrode array, the feedback received by the automated insertion tool may be analyzed in real time by the controller. This analysis may result in the modification or interruption of the minimum force trajectory based on the specific feedback that is received.

A second force curve (850) is shown as a dotted line and represents the average force profile of past surgeries under similar circumstances. For example, the average force profile may include surgeries of patients with a similar diagnosis who were implanted with a cochlear implant with the same design. This second force curve (850) provides guidance to the automated insertion tool and surgeon about the expected forces.

A third force curve (860) represents the actual force versus insertion depth profile for the current surgery. As illustrated by the third force curve (860), actual surgery profiles may have unique characteristics, but would be expected to generally follow the second force curve (850). When the third force curve (860) makes an unexpected deviation from the average force profile of past surgeries, as shown by the circled area (870), the automated insertion tool may take proactive steps to prevent the applied force from approaching the maximum allowable force profile (810). For example, the automated insertion tool may determine from the data represented by the actual force curve (860) that there is a substantial likelihood that, if the insertion is continued, the maximum applied force profile will be reached. The automated insertion tool can then make adjustments to reduce the amount of applied force required to continue the insertion. For example, the automated insertion tool may adjust the insertion angle or rotate the electrode. The actual force profile (860) shows that the adjustment was successful and the insertion force was significantly reduced following the adjustment.

The lower window (807) may also be useful in communicating the correct placement of the electrode within the cochlea. For example, as the automated electrode insertion tool approaches waypoint C, the insertion rate may be reduced to optimally place the electrode. If the electrode is over inserted, the automated electrode insertion tool could withdraw the electrode from within the cochlea to a required depth.

FIG. 8 is only illustrative of an exemplary embodiment of a screenshot of a display (800) which provides information about an ongoing or past electrode insertion procedure. Actual profiles and limits may vary according to the design of the cochlear implant, electrode insertion system, methods of measurement, and individual characteristics of the patient. For example, the force profiles could be split into various vectors that better describe the forces applied to the tissues within the cochlea. Further, the information presented in FIG. 8 show forces as measured in only one direction (e.g. forces applied axially on the tip of the lead or at some point along the lead). However, the insertion tool of the present embodiment may be configured to measure forces in any number of directions.

Figure 9:
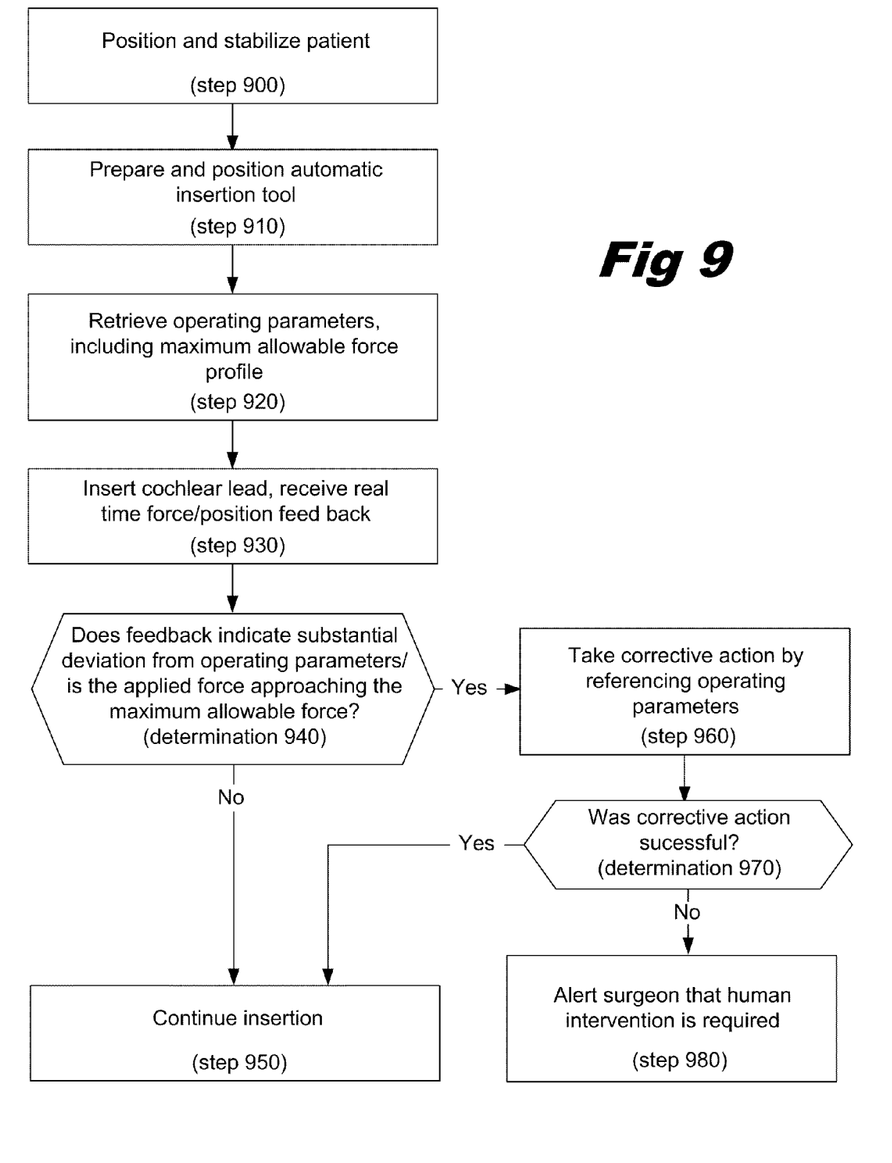
FIG. 9 is a flow chart showing one illustrative method for automated insertion of cochlear electrodes, according to one embodiment of principles described herein.

FIG. 9 represents one illustrative method for automated insertion of cochlear electrodes. According to one embodiment, the patient is first positioned and stabilized (step 900). The automated insertion tool is then prepared and appropriately positioned to begin the operation (step 910). The controller then retrieves or generates the operating parameters (step 920). By way of example and not limitation, these operating parameters may include: information about the cochlear lead (such as type, insertion depth, etc); information about the patient (such as diagnosis, age, sex); imaging or geometric data of the cochlea (from diagnostic imaging, historical library, etc.); information about the automated insertion tool (such as serial number, communication protocols); status of remote connections (such as connections to a remote surgeon, haptic device, or other control device); etc. Additionally, an average force profile and maximum force profiles may be retrieved or calculated.

The method may include additional steps that are not explicitly shown in FIG. 9. For example, there may be a number of diagnostic tests to determine if the system is operational and if a remote surgeon has the desired connection speed and control. Further, there may be a step that requires the authorization of the surgeon or other responsible person to proceed with the operation.

The operation then begins with the cochlear lead being inserted into the opening and the real time force and position feedback being received by the automated insertion device (step 930). As the insertion proceeds, there is a real time evaluation of the feedback to determine if there is a substantial deviation from the operating parameters (determination 940). For example, if the actual applied force approaches the maximum allowable force, this may trigger a determination that a substantial deviation has occurred. A variety of other events may trigger this determination. For example, a substantial deviation may occur if real time imaging indicates that the cochlear lead has an unexpected placement or if the insertion force is unexpectedly low. Either of these events could indicate that the wall of the cochlea has been perforated and corrective action is required.

If there is no substantial deviation from the expected profiles, the insertion continues (step 950) with feedback being continuously monitored.

If a substantial deviation does occur, the automated insertion tool will then take corrective action by referencing the operating parameters (step 960). For example, the operating parameters may include a list of commonly encountered issues and instructions for mitigating those issues. According to one embodiment, corrective action may include vibrating the electrode array via, for example, an ultrasonic vibrator that transmits vibrations to the distal end of the electrode array. According to other exemplary embodiments, corrective action may also include rotating the electrode array, slightly retracting the electrode array, or changing the insertion angle. The corrective actions of vibrating the electrode array, rotating the electrode array, retracting the electrode array, and changing the insertion angle of the electrode array may be performed manually by the surgeon or by the insertion tool (600, FIG. 6), and can be controlled manually or by mechanical means as presented above. In some circumstances, the operating parameters may include instructions that require the notification or authorization of surgeon to proceed.

If the corrective action was successful (determination 970), the insertion again continues (step 950). If the corrective action was not successful (determination 970), the surgeon is alerted that manual intervention is required (step 980). A number of additional steps may also be inserted. For example, the corrective action steps may be significantly more complex and the automated insertion tool may be instructed to perform a series of steps, with the insertion forces being checked throughout. If a first series of steps is unsuccessful in resolving the problem, a second series of steps may be automatically attempted, and so forth.

If the surgeon chooses to intervene, there are a number of options that can be pursued. By way of example and not limitation, the surgeon could then choose to: 1) insert no further, leaving the electrode at the present insertion depth, 2) attempt to use the ring-slider on the electrode insertion tool to advance the electrode, 3) provide or select alternative actions to the insertion tool from a menu or library, or 4) increase the maximal allowable force and either continue with a manual haptic insertion or reinitiate the automated insertion. Additionally or alternatively, the surgeon could disengage the automated insertion tool and proceed with a conventional insertion.

The instrumentation, systems, and methods described above could also be used with a number of other techniques. By way of example and not limitation, the automated insertion tool could be used in conjunction with improved lubrication and drug delivery techniques to improve patient outcomes and preserve residual hearing.

Further, the embodiments described above could be expanded to include more degrees of freedom in terms of control and positioning of the electrode around the cochleostomy. Each additional axis of motion could also be coupled to a force or torque sensor and incorporated into the automated insertion algorithm.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A method for insertion of a cochlear lead, comprising:
    generating a maximum allowable force profile from data recorded during a number of previous successful operations;
    selecting operating parameters comprising the maximum allowable force profile from a library of operating parameters;
    inserting said cochlear lead while sensing real time force and position;
    continuing said insertion while said real time force is below said maximum allowable force profile; and
    taking corrective action when the real time force approaches said maximum allowable force profile by matching said operating parameters, real time force, and position to a library of previous surgical data.

2. The method of claim 1, in which said step of inserting said cochlear lead comprises: controlling an insertion tool via a controller, controlling an insertion tool via a controller and via manual manipulation, controlling an insertion tool via manual manipulation, or combinations thereof.

3. The method of claim 1, further comprising:
    obtaining information comprising one or more of: the patient's diagnostic imaging, case history, and diagnosis;
    in which the selecting step comprises basing said maximum allowable force profile on the information.

4. The method of claim 1, in which said data recorded during a number of previous successful operations includes data comparing preoperative and postoperative residual hearing capability of the patients associated with said previous successful operations.

5. The method of claim 1, further comprising retrieving a minimum force trajectory from said library, said minimum force trajectory describing a multidimensional trajectory of said cochlear lead that is expected to require minimum insertion force.

6. The method of claim 5, further comprising taking corrective action if there exists a substantial deviation of said real time force from said minimum force trajectory.

7. A system for insertion of an electrode comprising:
    an insertion tool configured to insert said electrode into biological tissues; and
    a number of force sensors configured to provide data of real time forces applied in a number of directions by said electrode to said biological tissues,
    wherein said system is further configured to select operating parameters comprising a maximum allowable force profile from a library of operating parameters,
    wherein said maximum allowable force profile is generated from data recorded during a number of previous successful operations,
    wherein said insertion tool is configured to insert said electrode into biological tissues while said real time forces are below said maximum allowable force profile, and
    wherein said controller is configured to automatically select a corrective action when said real time forces approach said maximum allowable force profile by matching said operating parameters and real time forces and position to a library of previous surgical data.

8. The system of claim 7, further comprising a controller configured to control said insertion tool in which said controller selects said operating parameters.

9. The system of claim 7, in which said controller is further configured to insert said electrode while said force sensors sense said real time forces and position of said electrode, and continue insertion while said real time forces are below said maximum allowable force profile.

10. The system of claim 7, in which said maximum allowable force profile defines an insertion force based on insertion depth.

11. The system of claim 7, in which said controller is configured to provide for operating modes including fully automatic insertion of said electrode, semiautomatic insertion of said electrode and manual manipulation, manual insertion of said electrode with feedback, or combinations thereof.

12. The system of claim 7, in which said maximum allowable force profile is selected by the system based on a patient's diagnostic imaging, case history, diagnosis, or combinations thereof.

13. The system of claim 7, in which said data recorded during a number of previous successful operations includes data comparing preoperative and postoperative residual hearing capability of the patients associated with said previous successful operations.

14. The system of claim 7, in which said controller controls said insertion tool such that said electrode follows a minimum force trajectory in which said minimum force trajectory describes a multidimensional trajectory of said electrode that is expected to require minimum insertion force.

15. The system of claim 14, in which said controller is further configured to take corrective action if there exists a substantial deviation of said real time forces from said minimum force trajectory.

16. The system of claim 15, in which said controller is further configured to request human confirmation of said selected corrective action, accept human selection of said corrective action, direct human intervention via a haptic controller, or combinations thereof.

17. The system of claim 8, in which said data of said real time forces is conveyed through haptic feedback, visual feedback, audio feedback, or a combination thereof.

18. The system of claim 17, further comprising an audible indicator to convey said audio feedback that changes in pitch, amplitude, frequency, or combinations thereof.

19. The system of claim 8, further comprising a haptic controller, said haptic controller conveying an amplified representation of said data of said real time forces to a user, and generating instruction data directed to said insertion tool based on manipulation of said haptic controller by said user.

20. The system of claim 9, further comprising a visual display, said visual display conveying a maximum allowable force profile and data of said real time forces in which said visual display is further configured to display a representation of said biological tissues and representation of said electrode during insertion of said electrode into said biological tissues.

21. The system of claim 7, in which said electrode is an intracochlear electrode array.

22. The system of claim 7, further comprising a number of imaging devices configured to provide to said controller position data of said electrode within said biological tissues.

* * * * *